United States Patent [19]

Wheeler, Jr.

[11] Patent Number: 4,596,773
[45] Date of Patent: * Jun. 24, 1986

[54] STERILIZATION INDICATOR

[75] Inventor: Robert P. Wheeler, Jr., Keene, N.H.

[73] Assignee: Concord Laboratories, Inc., Keene, N.H.

[ * ] Notice: The portion of the term of this patent subsequent to Nov. 22, 2000 has been disclaimed.

[21] Appl. No.: 537,794

[22] Filed: Sep. 30, 1983

Related U.S. Application Data

[63] Continuation-in-part of Ser. No. 266,184, May 22, 1981, Pat. No. 4,416,984.

[51] Int. Cl.⁴ .................. C12Q 1/22; C12M 1/00; C12M 1/38; C12M 1/24
[52] U.S. Cl. ........................ 435/31; 435/287; 435/290; 435/296; 435/299; 435/300; 435/301
[58] Field of Search .............. 435/31, 287, 290, 296, 435/299, 300, 301

[56] References Cited

U.S. PATENT DOCUMENTS

| | | | |
|---|---|---|---|
| 2,854,384 | 9/1958 | Beakley et al. | 435/31 X |
| 3,239,429 | 3/1966 | Menolasino et al. | 435/31 X |
| 3,440,144 | 4/1969 | Andersen | 435/31 |
| 3,585,112 | 6/1971 | Ernst | 435/31 |
| 3,616,263 | 10/1971 | Anandam | 435/296 X |
| 3,657,073 | 4/1972 | Burton et al. | 435/31 X |
| 3,661,717 | 5/1972 | Nelson | 435/31 |
| 3,752,743 | 8/1973 | Henshilwood | 435/31 X |
| 3,875,012 | 4/1975 | Dorn et al. | 435/296 X |
| 4,215,198 | 7/1980 | Gordon | 435/31 |
| 4,291,122 | 9/1981 | Orelski | 435/31 |
| 4,304,869 | 12/1981 | Dyke | 435/296 |
| 4,416,984 | 11/1983 | Wheeler, Jr. | 435/31 |

Primary Examiner—Robert J. Warden
Assistant Examiner—Patricia Kate White
Attorney, Agent, or Firm—Sewall P. Bronstein; Robert M. Asher

[57] ABSTRACT

A sterilization indicator for testing the effectiveness of a sterilization process and a sterilization process using such an indicator are described. The indicator includes a container for holding a number of viable microorganisms and a quantity of nutrient medium; a separation member that prevents the nutrient medium from contacting the microorganisms; a penetration member that penetrates the separation member to allow the nutrient medium to contact the microorganisms and a cap, coupled to the penetration member, to seal the microorganisms and nutrient medium within the container.

27 Claims, 14 Drawing Figures

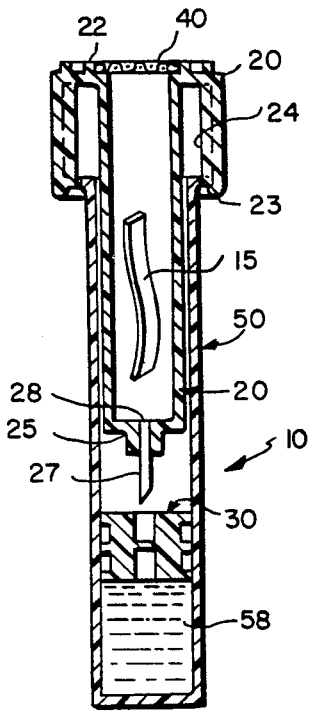
FIG.1
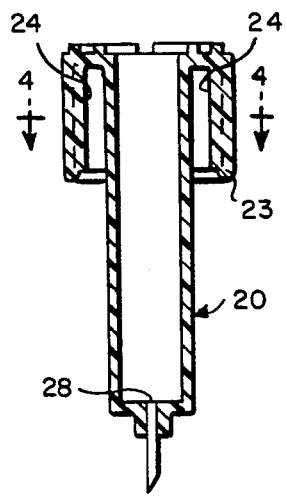
FIG.2
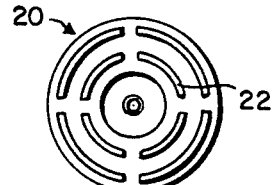
FIG.3
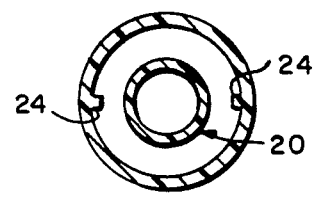
FIG.4
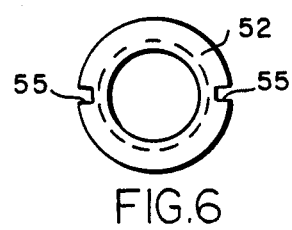
FIG.6
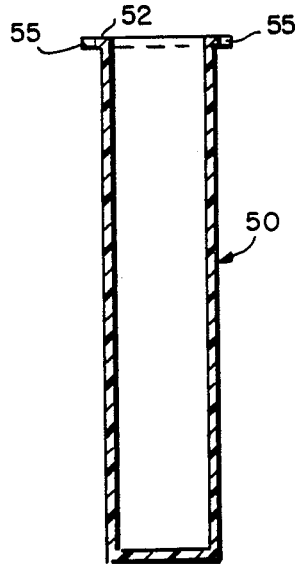
FIG.5
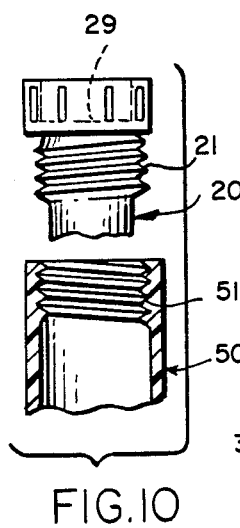
FIG.7
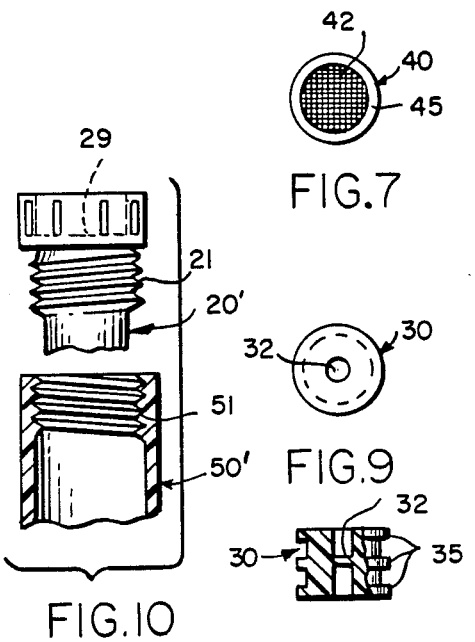
FIG.10
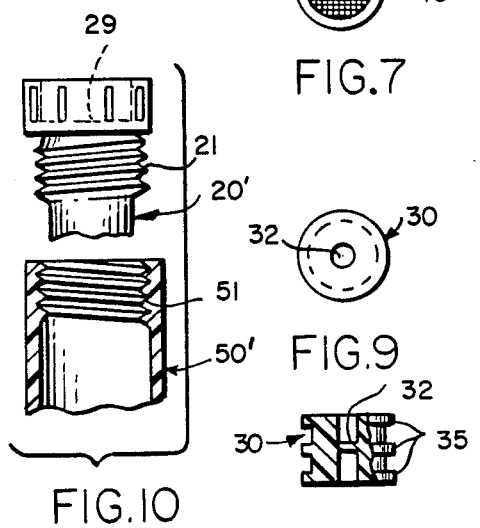
FIG.9
FIG.8

STERILIZATION INDICATOR

This application is a continuation-in-part of pending U.S. patent application Ser. No. 266,184, filed May 22, 1981, which has issued as U.S. Pat. No. 4,416,984.

FIELD OF THE INVENTION

This invention relates to an apparatus and method for checking and testing the effectiveness of sterilization, and particularly to an apparatus containing a sterilization indicator comprising bacterial spores or the like.

BACKGROUND OF THE INVENTION

In hospitals, clinics and the like, it has been standard practice to sterilize various products such as gowns, drapes, sheets, dressings, and other articles, prior to use by placing them in an autoclave where they are subject to steam sterilization. This practice is necessary to avoid infection and prevent contamination from the use of such articles where the same are not in a sterile condition and is particularly important where the articles have previously been used in the care of other patients.

Ethylene oxide sterilization is typically utilized in hospitals or laboratories for treating articles, for example of plastic, paper, rubber or the like which cannot withstand heat sterilization. Sterilization is effected when ethylene oxide reacts with contaminating microorganisms to kill or inactivate them.

Medical materials such as gauzes, bandages, or absorbent cotton, or surgical instruments such as injectors, scalpels, or scissors have hitherto been used after they have been sterilized with dry heat, pressure steam, or by boiling, using a sterilizer in the hospital. However, they have recently been supplied to users (such as hospitals and medical practioners) in a hermetically sealed sterilized style after they have been completely sterilized in the factory of the manufacturer for medical and surgical materials, instead of sterilizing them immediately prior to their use in hospitals or the like.

As there is no visual way of determining whether a particular article is sterile or not, it has been the practice to use a color change indicator with the article when placed in the steam sterilization chamber. The color change indicator changes under the sterilizing conditions of the autoclave, thus indicated that the particular article or package has been passed through the sterilizing cycle. The indicator may be in the form of a ribbon or card to which a color change ink has been applied.

However, even though such indicators show whether the materials have been exposed to the sterilization process, there is no indication of whether the process was effective. One way of determining whether or not sterilizing has been effective is to include in the sterilizer a biological test strip. Such a strip consists of a selected level of organisms having a resistance greater than is likely to be encountered on the articles being sterilized. Organisms that are particularly difficult to destroy are selected as the control standard, e.g., *Bacillus subtilis* var Niger and *Bacillus stearothermophilus*. After the sterilization cycle is completed, the strip is sent to the laboratory to determine if the organisms on the strip are dead thereby indicating sterilization effectiveness. While this method is reliable, it has the disadvantage of requiring several days or longer before the results are determined.

In addition to the time delay, the use of a biological test strip as an indicator has required a trained technician and clean room facilities for conducting the tests. In spite of all the precautions, using trained technicians and clean rooms, on occasion the tests are contaminated and false positives are obtained because of human error. The test must be considered positive and the product resterilized and retested causing delayed deliveries, increased costs, and the like.

However, the only way to be sure that the sterilization was effective is to run a biological test. Thus, improved tests are desired that would reduce or eliminate false positives and that would reduce or eliminate the requirement for trained technicians and or clean room environments for conducting the tests. Several attempts to provide a self-contained sterilization test have been described, for example, in U.S. Pat. Nos. 2,854,384; 3,068,154; 3,239,429; 3,346,464; 3,440,144 and 3,661,717. However, none of these solutions has provided an entirely satisfactory self-contained sterilization effectiveness test indicator.

SUMMARY OF THE INVENTION

The present invention provides a unitary sterilization indicator for determining the effectiveness of a sterilization process and a method for checking the effectiveness of a sterilization process using the indicator. The sterilization indicator of this invention comprises:

means for containing a number of viable microorganisms and a quantity of nutrient medium which promotes the growth of said microorganisms;

means for separating said nutrient medium from said microorganisms within said containing means until it is desired to contact said microorganisms with said nutrient medium;

means for penetrating said separating means to allow said nutrient medium to contact said microorganisms; and cap means, coupled to said penetrating means, for sealing said microorganisms and said nutrient medium within said containing means after said separating means has been penetrated.

BRIEF DESCRIPTION OF THE DRAWINGS

The invention may be more easily understood by reference to the accompanying drawings in which:

FIG. 1 is a partial cross-sectional view of one embodiment of an apparatus of the present invention including a culture strip;

FIG. 2 is a cross-sectional view of the inner compartment of FIG. 1 without culture strip;

FIG. 3 is a plan view of the compartment illustrated in FIG. 2;

FIG. 4 is a cross-sectional view of the compartment of FIG. 2 taken along lines 4—4 of FIG. 2;

FIG. 5 is a cross-sectional view of the outer compartment of FIG. 1;

FIG. 6 is a plan view of the compartment illustrated in FIG. 5;

FIG. 7 is a plan view of the closure disc of FIG. 1;

FIG. 8 is a partial cross-sectional view of the sealing member of FIG. 1;

FIG. 9 is a plan view of the sealing member of FIG. 8;

FIG. 10 is an expanded partial corss-sectional view illustrating a preferred embodiment of the invention;

DESCRIPTION OF THE INVENTION

Figure 11:
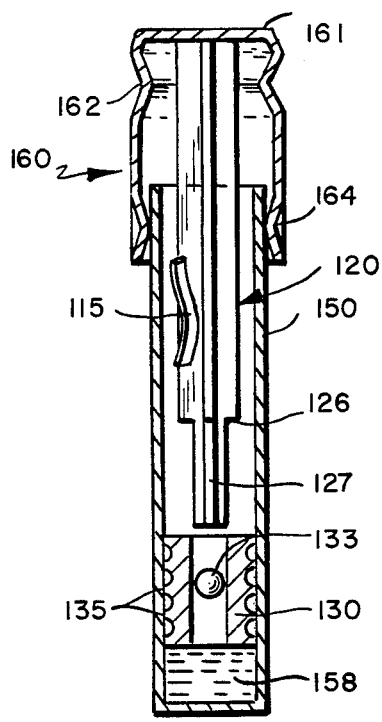
FIG. 11 is a cross-sectional view of a second embodiment of an apparatus of the present invention including a culture strip.

The sterility indicator of this invention may employ various microorganisms such as, for example, bacteria, fungi, protozoa and the like. Examples of specific bacteria that can be employed include *Bacillus subtilis, Bacillus stearothermophilus, Clostridium sporogenes,* etc. and the like. Examples of specific fungi that can be employed include Neurospora, Pithomyces, Daldinia, etc. and the like. Preferably, bacteria and fungi that exist in both "spore" and "vegetative" states are employed. Bacteria and fungi are commonly more resistant to sterilization in the spore state than in the vegetative state. Thus, to provide a margin of safety, bacteria and fungi in the spore state are preferably used in this invention. In selecting the particular microorganism to be used, a further margin of safety is provided by preferably employing microorganisms that are more highly resistant to the sterilization conditions than are the microorganisms intended to killed during the sterilization cycle.

The particular microorganism is selected, as aforesaid, in accord with the method of sterilization used such as heat, gas, radiation, etc. It should be appreciated that a single sterility indicator may contain more than one species of microorganism, each species being resistant to a different method of sterilization.

With reference to the figures, one embodiment of a sterility indicator in accord with the present invention is illustrated in FIG. 1. The sterility indicator 10 comprises a first compartment 20 partially surrounded by a second compartment 50 that is closed by engagement with the first compartment 20. The first compartment 20 is covered by a closure member 40 that is gas-permeable but impermeable to microorganisms.

Inside the first compartment 20 is located a strip 15 containing microorganisms of a species resistant to sterilization. Opposite the covered end is a partially open end that communicates with the second compartment 50 through opening 28. The partially open end of the first compartment 20 has a reduced diameter portion 25 adapted to engage a cannula 27. Alternately, the cannula 27 can be press-fit into opening 28 as illustrated in FIG. 2, or may be integrally molded with the first compartment 20.

One end of the first compartment 20 is adapted for receiving the open end of the second compartment 50 so that flange 52 of the second compartment engages the inward projecting flange 23 of the first compartment to join the compartments together.

The indicator components can be made from any suitable material. Plastics are preferred for ease of handling. It is desirable that clear materials be used so that the culture media can be readily seen to read the test results.

A sealing member 30 is inserted into the second compartment 50 providing a sealed chamber 58 for nutrient medium to promote the growth of the microorganism carried on the strip 15 contained in the first compartment 20. The sealing member 30 thus prevents the nutrient medium from premature contact with the microorganisms. The sealing member 30 has three circular ribs 35 that form the seal and stabilize it inside the second compartment. The sealing member 30 is also designed with a thin portion 32 that is easily engaged and punctured by the cannula 27 to provide access to the spore strip 15 for the nutrient medium contained in chamber 58. The sealing member can be made from any suitable elastomeric material that is not detrimentally affected by the sterilization process. The number of ribs 35 may be varied, for instance two or four ribs, or more, to provide adequate sealing.

Preferably, the sterility indicator is adapted with means for preventing activation so that the sealing member is not prematurely punctured. In the sterility indicator illustrated in FIG. 1, this is accomplished by providing one or more ribs 24, in this case two ribs, located on the first compartment 20 to prevent activating movement between the compartments and, thus, avoid premature puncturing of sealing member 30. When it is desired to activate the indicator by puncturing the sealing member, the ribs 24 are aligned with corresponding openings 55 in the flange 52 of the second compartment 50 and the seal can be readily punctured to allow communication between chamber and the first compartment 20 containing spore strip 15.

The sterility indicator 10 is assembled by filling a predetermined quantity of nutrient medium for the microorganism into the second compartment 50. Any suitable nutrient medium for the microorganism can be used. An example of a suitable nutrient medium is Tryptic Soy Broth. Other suitable media are well known to those skilled in the art.

After the nutrient medium is placed in the second compartment 50, the sealing member 30 is inserted a sufficient distance so that the first compartment 20 can be inserted and engaged with the second compartment through the coupling of flanges 23 and 52 without puncturing the thin portion 32 of the sealing member.

After sterilization of the partially assembled indicator, a spore strip 15 carrying a resistant microorganism is inserted in the first compartment 20 and closure 40 is snapped into ring 22. The closure 40 comprises an annular ring 45 holding a material 42 that is gas-permeable and/or steam-permeable (for steam sterilization) but impermeable to microorganisms. The material preferably is selected from filter media capable of filtering out microorganisms while allowing the transmission of gases. Filter materials having ratings less than 0.5 $\mu$m are preferred, and membrane materials are particularly preferred. Alternatively, a filter comprised of a suitable depth of cotton or synthetic fiber can be used. One-eighth inch thickness of material having a 10 micron rating has been found satisfactory.

In the practice of this invention the microorganisms are preferably carried on an absorbant material. Filter paper is particularly useful as the carrier. However, pieces of material simulating particular products to be sterilized may be preferred as the carrier in some circumstances.

A detector composition is contained in one of the compartments of the sterility indicator. The detector composition is a composition that undergoes a detectable change in response to the growth of the microorganisms. Preferably the detectable change is a visible change such as a change in color so that the change is readily apparent to an unskilled observer. However, other detectable changes requiring instrumentation are useful, particularly in automated operations.

If the detector composition is to be placed in the second compartment, it is added to the nutrient medium and sterilized with the partially assembled indicator as described above. If the detector composition is to be placed in the first compartment it can be added separately or carried on the spore strip.

Suitable detector compositions are well known in the art and are selected depending on the biological process expected from the particular microorganism and nutrient medium used in the test. Typically, as microorganisms such as bacteria metabolize, the pH drops due to acidic metabolic products and the production of $CO_2$. Thus suitable pH indicators such as Brom Thymol Blue, Methylene Blue, Bromocresol Purple, Phenol Red, and the like, etc. can be used depending on specific conditions.

Because bacteria reach a stationary phase in which growth is regulated by limiting factors such as growth nutrients, dissolved oxygen, etc., the bacteria die and lyse releasing alkaline endotoxins and cell constituents. This shifts the pH alkaline resulting in false negatives. Combinations of indicators such as Brom Thymol Blue and Phenol Red have been found to overcome this problem.

It has also been found that adding glucose to the Tryptic Soy Broth medium tends to increase acid production and enhance the color transition.

In use the sterilization indicator in accord with the present invention is placed in the sterilization chamber along with the materials and/or objects being sterilized and the sterilization cycle is completed. The sterilization chamber is then unloaded and the sterilization indicator is activated by aligning ribs 24 with openings 55 in flange 52 and the two compartments are moved axially with respect to each other so that the thin portion 32 of sealing member 30 is pierced by cannula 27 and chamber 58 is open to the first compartment 20. Instead of providing a thin portion 32 in the sealing member, a ball bearing or other plug may be used to seal the passageway. This plug is pushed out by engagement of the cannula with the sealing member to open communication between compartments. Nutrient medium can then flow from chamber 58 into compartment 20 to contact the spore strip 15 and promote the growth of any viable microorganisms.

In another embodiment as illustrated in FIG. 10, the first compartment 20' and second compartment 50' are each provided with threaded portions 21 and 51, respectively. After the sterilization cycle this preferred indicator is activated by turning the first compartment 20' into the second compartment 50' by means of threaded portions 21 and 51, thus causing the thin portion 32 of sealing member 30 to be punctured. The top portion of compartment 20' is formed with a chamber 29 which will hold a depth filter.

A cap may be provided with the sterilization indicator 10 so that the end of the first compartment 20 can be closed in order to prevent the medium from evaporating during incubation. Preferably the cap is attached to the second compartment 50 by means of a tether or the like so that the cap cannot be separated from the indicator unit or lost. In addition, attaching the cap to the second compartment provides a means to prevent closure of the first compartment until after activation of the indicator unit by selecting the appropriate length for the tether.

The activated sterility indicator is then incubated for a predetermined length of time depending on the particular sterility specifications being met. After incubation the sterility indicator is examined for any detectable change indicated by the detector composition as a result of the growth of microorganisms that survived the sterilization cycle. If any detectable change is found the sterilization cycle must be repeated.

Referring now to FIGS. 11 through 14, a preferred embodiment of a sterility indicator of the present invention is illustrated. Parts of this indicator which correspond to parts of the indicator of the first embodiment are identified by numbers 100 greater than their counterpart. The structure of this second indicator differs from the first embodiment, however, it is used in the same way. The above description of appropriate microorganisms, detector composition and nutrient medium for use in a sterilization indicator apzplies to both embodiments.

The second embodiment comprises a container 150. The nutrient medium 158 is located in a portion of the container 150 at its bottom. A ring-shaped stopper 130 or sealing member separates the nutrient medium from the remainder of the container 150. The hole through the center of the ring-shaped stopper 130 accommodates a ball 133 which acts to plug the hole. Thus the ball 133 and the stopper 130 act to seal and separate the nutrient medium from the remainder of the container 150. The ring-shaped stopper in this preferred embodiment has five circular ribs 135 to contribute to the sealing function. The stopper ca also be made as illustrated in FIG. 8.

A spore strip 115 carrying the microorganisms must be placed in the part of the container 150 separated from the nutrient medium. The spore strip 115 may be attached to either the container 150 or preferably carried on a plunger 120. The plunger 120 move axially within the container 150. The plunger includes two functional parts—a shoulder 126 and an elongated cross-shaped member 127. The cross-shaped member 127 penetrates the hole in the stopper 130 to push the ball 133 out of the hole. Thus, the nutrient medium can move through the open areas between the cross of the elongated member 127 to pass into the remainder of the container 150 and contact the spore strip 115. To help get the nutrient medium out of the bottom portion of the container 150, the shoulder 126 pushes against the stopper 130. As the stopper 130 is forced downward the nutrient medium is forced upward through the hole. As in the first embodiment, the detector composition may be placed in the nutrient medium, on the spore strip 115 or somewhere else inside the container 150.

Figure 12:
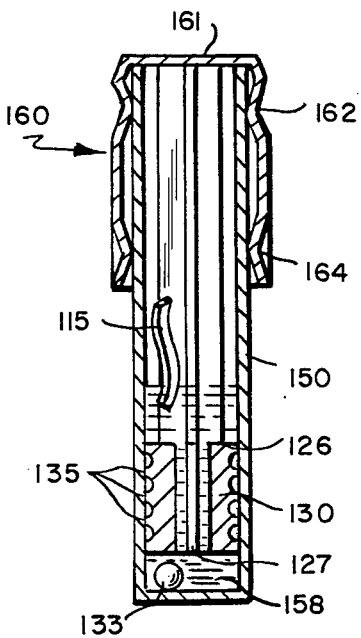
FIG. 12 is a cross-sectional view of the apparatus of FIG. 11 after the separation member has been penetrated and the container sealed.
Figure 13:
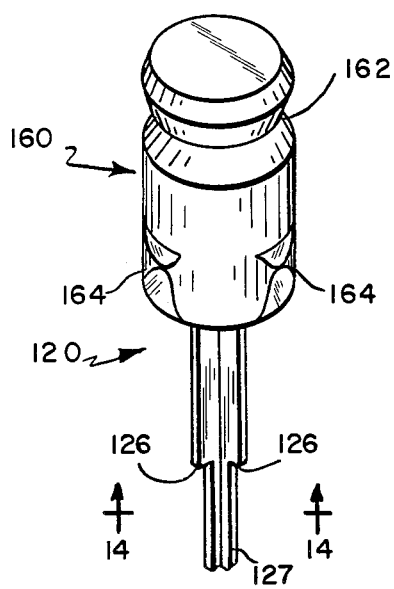
FIG. 13 is a perspective view of the plunger and cap of the apparatus of FIG. 11.
Figure 14:
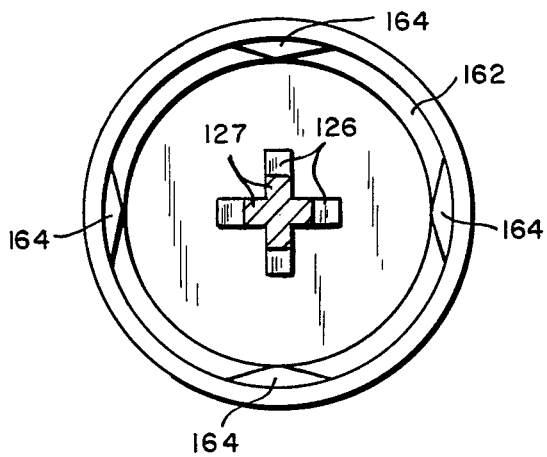
FIG. 14 is a cross-sectional view of the plunger and cap taken along lines 14—14 of FIG. 13.

Connected to the top of the plunger 120 is a cap 160. When the plunger 120 is fully depressed into the container 150 the cap seals the container. This prevents the medium from evaporating during incubation. It also prevents microorganisms from entering the container 150 and contaminating the indicator after sterilization. The seal may be formed between the top of the cap 161 and the top rim of the container 150. A seal is also formed by an indented annulus 162 about the top of the cap and the side of the container 150. These seals form when the cap is fully depressed into the container, as shown in FIG. 12. FIG. 12 shows the sterilization indicator during the incubation period. Suitable resilient materials can also be used to form the seal, as is well known in the art.

When the sterilization indicator is to be placed into a sterilization chamber with the other objects and materials to be sterilized, it will appear as in FIG. 11 with the ball 133 intact within the stopper 130. The plunger 120 is held in place either by the cross-shaped elongated member 127 as it sits within the very top portion of the hole of the ring-shaped stopper 130 and/or by a set of positioning indentations 164. The indentations 164 are located about the cap 160 beneath the annulus 162 and extend flush against the side of the container 150 thus holding the plunger 120 against the container 150 when in the open position shown in FIG. 11. The indentations 164 are used rather than an annulus so that gases are allowed to flow into the container 150 around the indentations 164. Thus, in the open position shown in FIG. 11 air and ethylene oxide can pass through the passages between the indentations 164 and up into the container 150. In this manner the spore strip 115 during the sterilization process is fully exposed to the sterilization chamber. It would also be possible to change the cap structure by including holes in the sides which would serve the function of allowing air into the container when the plunger is in the open position.

After the sterilization indicator has been in the sterilization chamber, one movement will cause the elongated member 127 to penetrate through the ring-shaped stopper 130 to allow nutrient medium into the remainder of the container to contact the microorganisms on the spore strip 115. To facilitate the contact between the medium and the microorganisms, the shoulder 126 at the same time pushes down on the stopper 130 to force the nutrient medium up into the rest of the container 150. Also, as a result of this one movement the indented annulus 162 comes in contact with the side of the container 150 to seal off the incubating microorganisms on the spore strip 115 from the atmosphere.

Although the invention has been described in detail with reference to the preferred embodiments thereof, it will be appreciated that those skilled in the art, upon reading this disclosure, will be enabled to make modifications and improvements within the spirit and scope of this invention. For instance, other geometric and structural configurations for the plunger, container and separating member can be readily adapted to practice the invention by those skilled in the art. These and other changes can be made without departing from the spirit and scope of the invention and without diminishing its attendant advantages. It is therefore intended that such changes and modifications be covered by the following claims.

What is claimed is:
1. A sterilization indicator comprising:
   means for containing a number of viable microorganisms and a quantity of nutrient medium which promotes the growth of said microorganisms;
   a stopper forming a seal within said containing means to enclose said nutrient medium in a portion of said containing means separate from said microorganisms until it is desired to contact said microorganisms with said nutrient medium;
   means for penetrating said stopper to allow said nutrient medium to contact said microorganisms; and
   cap means, coupled to said penetrating means, for sealing said microorganisms and said nutrient medium within said containing means after said stopper has been penetrated.

2. The sterilization indicator of claim 1 wherein said penetrating means comprises an elongated member having an end with cross-section in the shape of a cross.

3. The sterilization indicator of claim 1 wherein said stopper is ring-shaped with removable plug means for filling the hole in said stopper.

4. The sterilization indicator of claim 3 wherein said plug means comprises a ball.

5. The sterilization indicator of claim 3 wherein said penetrating means comprises an elongated member having an end for pushing said plug means out of said stopper.

6. The sterilization indicator of claim 5 wherein said elongated member includes a shoulder of greater cross-section than said end for pushing against said stopper after said plug means has been pushed out of said stopper, so that said nutrient medium is forced through the hole of said stopper.

7. A sterilization indicator comprising:
   means for containing a number of viable microorganisms and a quantity of nutrient medium which promotes the growth of said microorganisms;
   separation means for enclosing said nutrient medium within a portion of said containing means to separate said nutrient medium from said microorganisms until it is desired to contact said microorganisms with said nutrient medium;
   an elongated member for penetrating said separation means to allow said nutrient medium to contact said microorganisms;
   plunger means, connected to said elongated member, for pushing against said separation means to move said separation means relative to said containing means so as to reduce the size of said portion of said containing means and to force said nutrient medium out of said portion of said containing means and into contact with said microorganisms; and
   cap means, coupled to said plunger means, for enclosing said microorganisms and said nutrient medium within said containing means after said separating means has been penetrated.

8. The sterilization indicator of claim 7 wherein said containing means further contains a detector composition capable of undergoing a detectable change in response to the growth of said microorganisms.

9. The sterilization indicator of claim 8 wherein said detector composition undergoes a visible change in response to the growth of said microorganisms.

10. The sterilization indicator of claim 9 wherein said visible change is a change of color.

11. The sterilization indicator of claim 7 wherein said separation means includes a ring-shaped stopper and a ball axially movable within the hole through said stopper, said ball being the size necessary to plug the hole in said stopper.

12. The sterilization indicator of claim 7 wherein said cap means further includes means for holding said elongated member and said plunger means in place within said containing means before said separation means has been penetrated, said holding means including means for allowing air to pass into said containing means.

13. The sterilization indicator of claim 12 wherein said holding means comprises a plurality of indentations.

14. A sterilization indicator comprising:
   means for containing a number of viable microorganisms and a quantity of nutrient medium which promotes the growth of said microorganisms;
   separation means for enclosing said nutrient medium within a portion of said containing means to separate said nutrient medium from said microorganisms until it is desired to contact said microorganisms with said nutrient medium;

a plunger inserted within said containing means, said plunger including penetration means, at one end thereof, for penetrating said separation means to allow said nutrient medium to contact said microorganisms and said plunger including shoulder members extending from said penetration means to push against said separation means to move said separation means relative to said containing means so as to reduce the size of said portion of said containing means and to force said nutrient medium out of said portion of said container and into contact with said microorganisms after said separation means has been penetrated;

a cap connected to the plunger at the opposite end of said penetration means, said cap sealing said containing means when said plunger has been fully inserted into said containing means; and means, connected to said cap, for holding said plunger partially inserted within said containing means, said holding means including means for allowing air to pass into said containing means.

15. The sterilization indicator of claim 14 wherein said holding means comprises a plurality of indentations in said cap.

16. The sterilization indicator of claim 14 wherein said containing means further contains a detector composition capable of undergoing a detectable change in response to the growth of said microorganisms.

17. The sterilization indicator of claim 16 wherein said detector composition undergoes a visible change in response to the growth of said microorganisms.

18. The sterilization indicator of claim 17 wherein said visible change is a change of color.

19. The sterilization indicator of claim 14 wherein said separation mean includes a ring-shaped stopper and removable plug means for filling the hole in said stopper.

20. The sterilization indicator of claim 19 wherein said plug means comprises a ball.

21. The sterilization indicator of claim 19 wherein said ring-shaped stopper is an elastomeric stopper.

22. The sterilization indicator of claim 14 wherein said penetration means comprises an elongated member having an end with a cross-shaped cross-section.

23. The sterilization indicator of claim 14 wherein said microorganisms are carried on a substrate.

24. The sterilization indicator of claim 23 wherein said substrate is carried on said plunger.

25. The sterilization indicator of claim 23 wherein said substrate is an absorbent material.

26. A method for checking the effectiveness of a sterilization process, said method comprising:

placing a sterilization indicator into a sterilization chamber along with objects to be sterilized, said sterilization indicator comprising means for containing a number of viable microorganisms and a quantity of nutrient medium which promotes the growth of said microorganisms; a stopper forming a seal within said containing means to enclose said nutrient medium in a portion of said containing means separate from said microorganisms until it is desired to contact said microorganisms with said nutrient medium; means for penetrating said stopper to allow said nutrient medium to contact said microorganisms; and cap means, coupled to said penetrating means, for sealing said microorganisms and said nutrient medium within said containing means after said stopper has been penetrated;

including a detector composition within said containing means, said detector composition being capable of undergoing a detectable change in response to the growth of said microorganisms;

removing the sterilization indicator from the sterilization chamber along with the objects being sterilized after completion of the sterilization cycle;

penetrating said stopper to allow said microorganisms to contact the nutrient medium;

sealing said microorganisms and said nutrient medium within said containing means;

incubating the sterilization indicator for a predetermined period of time of promote the growth of the microorganisms; and examining the sterilization indicator for said detectable change in response to the growth of the microorganisms.

27. The method for checking the effectiveness of a sterilization process according to claim 26 wherein said detector composition undergoes a visible color change and the examining step comprises visual examination of the indicator to determine whether any color change has occurred.

* * * * *